United States Patent [19]

Sandhu et al.

[11] Patent Number: 5,796,003
[45] Date of Patent: Aug. 18, 1998

[54] ACOUSTIC IMAGING SYSTEMS

[76] Inventors: Jaswinder S. Sandhu, 454 Carman Ave., Buffalo Grove, Ill. 60089; Witold J. Popek, 500 W. Huntington Commons, Apt. 348, Mount Prospect, Ill. 60056; Honghui Wang, 1529 S. Wolf Rd., Apt. F-7, Prospect Heights, Ill. 60070

[21] Appl. No.: 594,040

[22] Filed: Jan. 30, 1996

[51] Int. Cl.[6] .................................................. G01N 29/06
[52] U.S. Cl. ........................................................... 73/603
[58] Field of Search .............................. 73/603, 606, 618

[56] References Cited

U.S. PATENT DOCUMENTS

| | | | |
|---|---|---|---|
| 4,338,821 | 7/1982 | Dion | 73/603 |
| 4,530,242 | 7/1985 | Sandhu | 73/603 |
| 4,651,567 | 3/1987 | Sandhu | 73/606 |
| 4,679,436 | 7/1987 | Sandhu | 73/606 |
| 5,329,817 | 7/1994 | Garlick et al. | 73/603 |

*Primary Examiner*—John E. Chapman

[57] ABSTRACT

An ultrasonic inspection system for inspecting a test object and producing substantially artifact-free images, which system includes (1) a sound source for emitting ultrasonic energy toward a test object, (2) a liquid crystal detector for detecting emitted ultrasonic energy and displaying an image, and (3) a coupling medium for sonically coupling the sound source, the test object and the detector. The ultrasonic energy is emitted at each of a plurality of frequencies within a predetermined range. It has been determined that the ultrasonic energy insonifing the object can be caused to scan the object and be angularly varied with respect thereto. Moreover, the rate of frequency scanning is substantially less that the detector image decay so as to produce a substantially flicker-free image. The angular variation is performed by rocking the sound source through a small angle, such as 2° to 6° relative to the liquid crystal detector. Desirably the pivot axis about which the sound source is rocked falls within the body of the sound source or locus of points through which the sound source is moved. This rocking action minimizes disturbance of the coupling medium.

8 Claims, 3 Drawing Sheets

ACOUSTIC IMAGING SYSTEMS

BACKGROUND OF THE INVENTION

This invention relates to acoustic imaging systems that employ liquid crystal detectors, and more particularly, to improved processes and means for generating higher quality images than available previously.

Generally speaking, such systems employ a sound source for irradiating a test object with acoustic/ultrasonic waves. Upon traversing the object, the waves are differentially attenuated (due to reflection, refraction, scattering, and absorption) and form a shadow image which is converted into a visual image by the liquid crystal detector (i.e., a thin layer of liquid crystal material encapsulated by and between appropriate cell covers). The sound source liquid crystal detector, and test object are acoustically coupled, usually in a water tank, although alternative methods of coupling may be provided, such as by gels, oil impregnated rubbers, bubblers, squirters, etc. Additionally, the systems may include acoustic lenses for image formation, a reference sound source for holographic image formation, and various optical arrangements for viewing the liquid crystal detector.

Examples of the acoustic imaging systems described above are found in the prior art patents or publications such as Dreyer U.S. Pat. Nos. 3,597,043 and 3,991,606; Kessler et. al. U.S. Pat. No. 3,707,323; Greguss U.S. Pat. No. 3,831,434; Mailer U.S. Pat. No. 3,837,434; Dion U.S. Pat. No. 4,338,821; Sandhu U.S. Pat. No. 4,379,408; and Sandhu U.S. Pat. Nos. 4,530,242 and 4,641,567. Discussion of such systems is also found in various published articles such as Candau et. al. "Ultrasonic Propagation in Liquid Crystals", Advances in Liquid Crystals, Academic Press, 1978; Kapustina et. al. "Experimental Investigation of Liquid Crystal Acousto-optical Image Converter", Sov. Phys., Acoust., Vol. 22, No. 3, 1977; Dion et. al. "Ultrasonic Intensity and Phase Imaging at 3.6 MHz using Liquid Crystal Conversion", IEEE Transactions, Vol. UFFC-34, No. 5, 1987; and Kapustina "Acousto-optical Phenomena in Liquid Crystals", Mol. Cryst. Liq. Cryst., 1984, Vol. 112, pp. 1–164.

In general, the quality of images produced by the prior art systems is often degraded by the presence of interference artifacts such as "speckle" and "ringing". "Speckle" refers to randomly positioned variations in image intensity due to phase cancellations and reinforcements. "Ringing" refers to systematic variations, also due to phase cancellations and reinforcement, and usually appears as fringes in the images. Such artifacts can make the image difficult to interpret.

Therefore, it is an object of this invention to provide means for minimizing and/or for removal of these artifacts or to prevent them from forming.

The prior art describes several attempts for circumventing problems caused by the interference artifacts believed to result from the wave coherence. For example, Dion, U.S. Pat. No. 4,338,821, has used phase shifting through a swinging-like movement of the acoustic transducer (sound source) to reduce interference artifacts. However, the physical movement of the acoustic transducer, as disclosed by Dion, is undesirable because (1) it necessitates the use of complex mechanical equipment and (2) it may significantly disturb the coupling medium and thus disturb other components of the acoustic imaging system. Moreover, the Dion system has not produced a high-quality, substantially artifact-free image on a liquid crystal detector.

Sandhu, U.S. Pat. No. 4,651,567, disclosed frequency shifting and phase shifting of a transducer (sound source) mounted in a pendulum-like sector scanning apparatus to reduce the interference artifacts. The physical movement of the transducers is undesirable for reasons cited in the preceding paragraph.

Another object of this invention is to provide an acoustic imaging system in which the sound source motion produces minimal disturbances in the coupling medium and is accomplished through a simpler scanning apparatus.

These and other objects of this invention will become apparent from the following disclosure and appended claims.

SUMMARY OF THE INVENTION

There is disclosed herein an improved acoustic imaging system where an improved method and means are provided to generate sound source motion which minimizes disturbances to the coupling medium and allows production of a high-quality image substantially free of image artifacts. In the system the sound source, object to be inspected and liquid crystal detector are all ultrasonically coupled. The sound source generates sound over a frequency range (bandwidth) where the range is selected to minimize interference effects due to wave coherence. In other words, the frequency is scanned between the range limits. The ultrasonic energy is formed in a beam-like configuration. The beam is also angularly varied, with respect to the liquid crystal detector over a small angle which enhances image formation and minimizes artifact formation and distortion. In this system the sound source is rocked or pivoted about a pivot point or axis which falls within the body of the sound source and through a relatively small angle, so as to minimize disturbance of the coupling medium.

DESCRIPTION OF THE PREFERRED EMBODIMENT

In General

Figure 1:
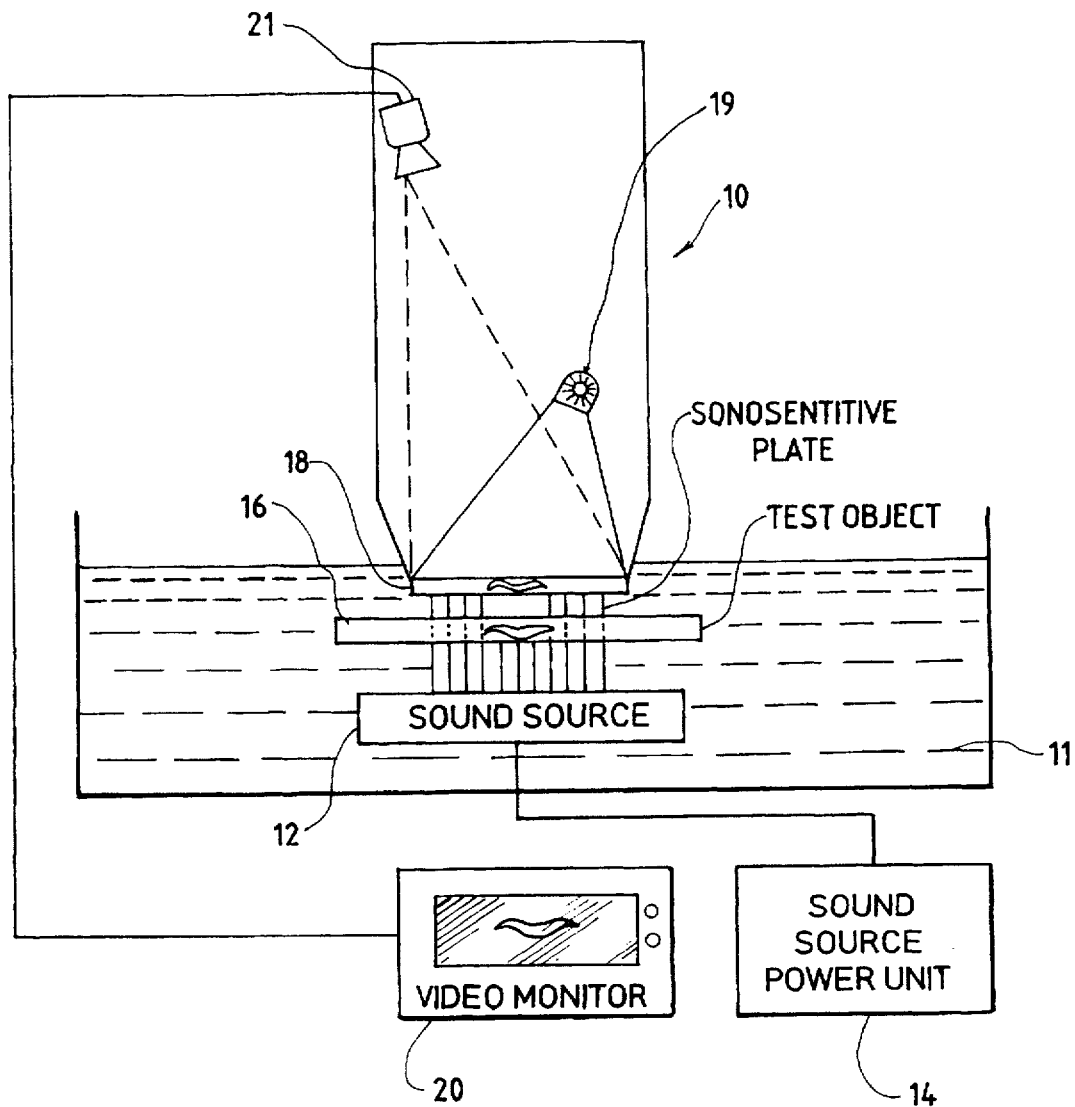
FIG. 1 is a block-style diagram of the system of this invention.

Referring now to FIG. 1, there is shown an acoustic imaging system 10 generally which can be vertically oriented. A liquid bath 11 (usually water) is provided for coupling and within which a sound source 12 is immersed. The source 12 is connected to a power source 14. An object 16 to be imaged is disposed in the bath and is thus acoustically coupled to the sound source and the object is arranged to be irradiated by the sound source. A liquid crystal detector 18 (sometimes referred to as a sono-sensitive plate) receives the acoustic energy which passes through the object and converts it to an optical image. A typical detector includes a liquid crystal layer disposed between and encapsulated by a pair of outer covers or layers. The layers are optically and/or sonically transparent. The liquid crystal detector 18 and the acoustic image thereupon are illuminated by a polarized light source 19 and may be viewed on a TV monitor 20 using a video/CCD camera 21, which also includes a polarizer.

Frequency & Angular Scanning

Figure 2:
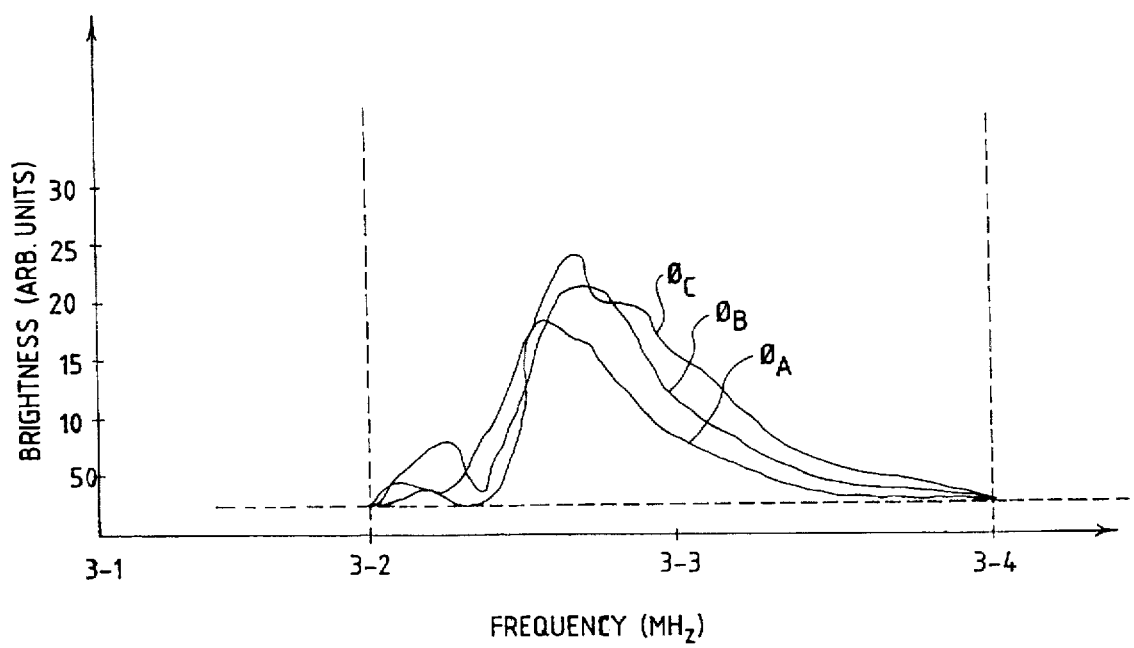
FIG. 2 is a stylized view depicting the acousto-optical response (sometimes referred to as the brightness) of the liquid crystal detector as a function of frequency over an angular scanning range.

The minimization of speckle and ringing is achieved by simultaneous scanning of the sound source frequency and beam angle variation. The frequency range is determined by the acousto-optical characteristics of the liquid crystal detector. In FIG. 2, the acousto-optical response of a liquid crystal detector is shown as a function of frequency for a range of beam angles. In FIG. 2, $\ominus A=6°$, $\ominus B=5°$ and $\ominus C=4°$. The frequency range is selected to be the range outside of which (1) little or no acousto-optical response is detected and (2) no significant reduction in speckle or ringing is detected if the range is increased. For the specific liquid crystal detector shown in FIG. 2, the frequency scanning range was determined to be from about 3.2 MHz to 3.4 MHz. The frequency scanning time is kept small compared with the response time of the liquid crystal detector so that an integrated image is seen without flicker. For the specific liquid crystal detector shown in FIG. 2, the frequency scanning time was less than 1 second.

The angular range of the sound source is determined similarly to the frequency range, i.e. the range outside of which (1) little or no acousto-optical response is detected and (2) no significant reduction of speckle is achieve if the range is increased. For the specific liquid crystal detector, the angular range was determined to be generally between 2° and 6°. This small angular range can be achieved with only a slight rocking motion of the sound source, which minimizes disturbance in the coupling medium. Here the rocking motion can be thought of as a pivot axis which passes through the body of the sound source. The rocking motion can be in a single plane or the transducer can be rotated so that rocking occurs over 360° and in a sense the beam of ultrasonic energy forms a cone or conical shape with the transducer at the apex and the liquid crystal detector at the base.

Figure 3:
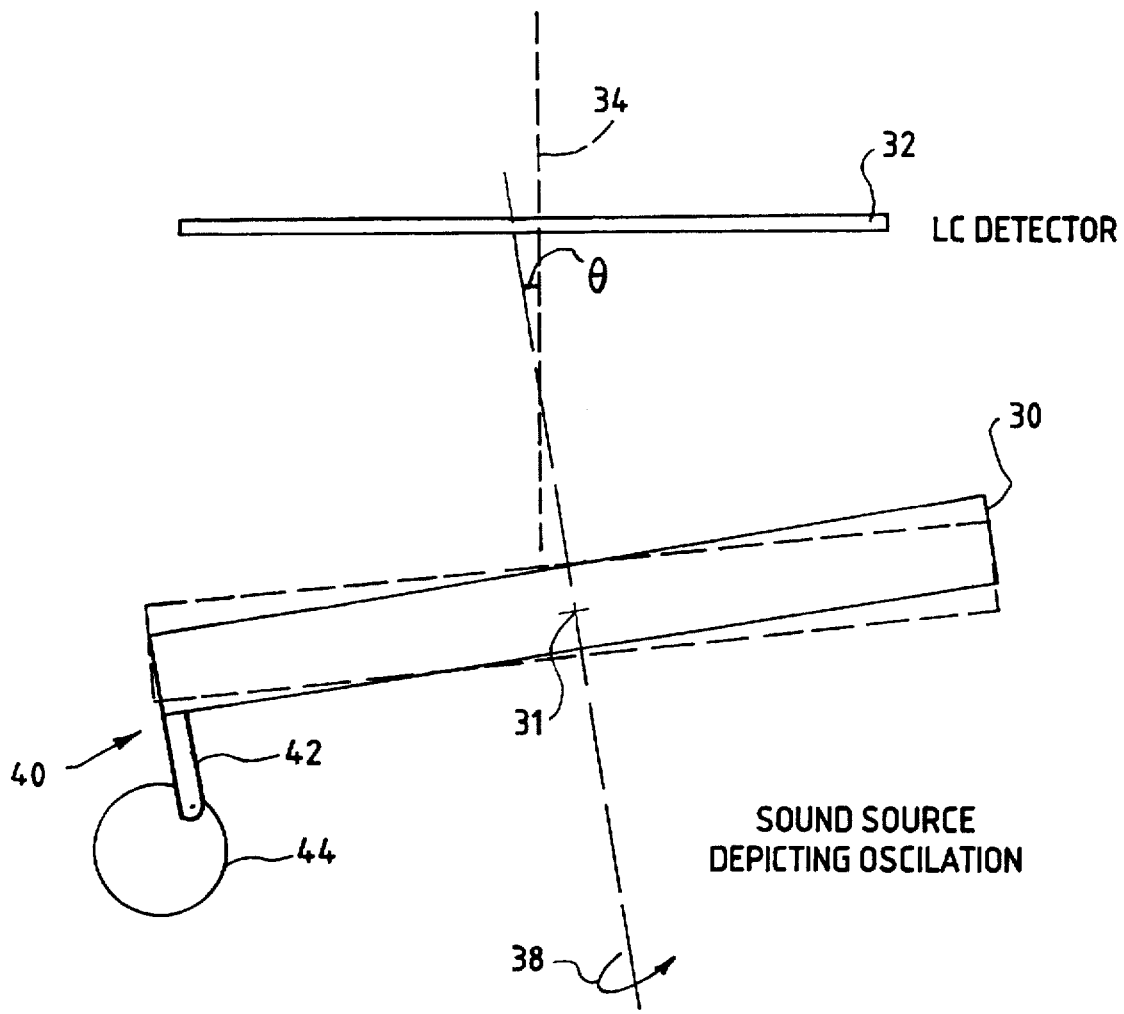
FIG. 3 is a diagrammatic view of an angle scanning system.

Referring more specifically to FIG. 3, a sound source or transducer 30 is shown with the pivot axis 31. The transducer is oriented obliquely to a liquid crystal detector 32. Another way of looking at this arrangement is that the normal 34 to the detector intersects the normal 36 to the sound source at a small angle $\ominus$. During the rocking motion the angle $\ominus$ various between $\ominus 1$ and $\ominus 2$ which is a small angle of about 2° to 6°.

The rocking motion may be achieve by many different mechanisms.

Shown herein is a single eccentric system 40 where a link 42 and a rotating drive wheel or disc 44 are provided. The link is connected at one end to the sound source and at the other end to the drive wheel. Rotation of wheel 44 causes the link to move and thus the sound source to rock.

If desired, the sound source can also be caused to rotate, as suggested by arrow 38, about the normal. Thus the sound source can rock through its 2° to 6° range, either in a plane or while rocking the unit can rotate up to 360°. Mechanisms 39 for rotation are known in the art.

Figure 4:
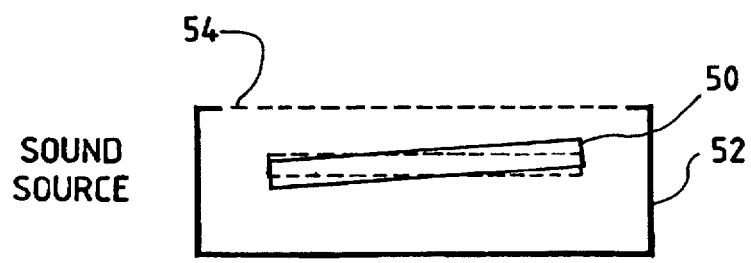
FIG. 4 is also a diagrammatic view showing the sound source contained in a housing.

In a modified embodiment, see FIG. 4, the rocking sound source 50 is enclosed in a housing 52. The housing includes a window portion 54 which is transparent to ultrasonic energy so the beam of energy can be directed at an object to be inspected and the image then directed to a liquid crystal detector. The housing is provided to further minimize disturbance of the coupling medium due to the rocking movement of the sound source while not adversely affecting the ultrasonic performance of the unit.

For the specific liquid crystal detector, the angular scanning time was less than 1 second to minimize image flicker.

It is believed that this angular variation can also be achieved electronically using beam steering techniques of the type used in medical transducers. This could eliminate the need for mechanical motion apparatus.

The foregoing procedures provide improved and substantially artifact-free ultrasonically produced images of the test object with minimal disturbances to the coupling medium due to sound source motion.

It will be appreciated that numerous changes and modifications can be made to the embodiments disclosed herein without departing from the spirit and scope of this invention.

What is claimed is:

1. A non-destructive inspection system for forming a substantially artifact-free image of a test object, which system includes:

a source of ultrasonic energy to be directed at a test object;

a liquid crystal detector for receiving ultrasonic energy exiting the test object and providing a visual display for an image;

a medium for coupling the source test object and the detector;

a first device for moving said source about a fixed pivot that is substantially within said source, whereby the normal to the source is caused to move through a small angle relative to the liquid crystal detector which minimizes disturbance of the medium due to movement of the source and cooperates in assuring an artifact-free image; and a second device for exciting said source so as to cause ultrasonic energy therefrom to oscillate between a pair of predetermined frequencies and scan the frequencies therebetween in a period of time sufficiently short so as to provide a flicker-free image; and wherein said first device for moving includes rotatable disc and a link connected to the source and eccentrically connected to the disc.

2. A system as in claim 1 and further including a housing within which the source and first device are enclosed so as to minimize coupling medium disturbance from the movement of the source and which housing includes a window portion which is transparent to ultrasonic energy so that an ultrasonic beam can be directed from the source to a position outside the housing.

3. A system as in claim 1, wherein the normal is caused to move through a small angle relative to the liquid crystal detector between about 2° to 6°.

4. A system as in claim 1, wherein a detector defines a normal and said source normal and detector normal are oblique to each other and intersect at a small angle.

5. A system as in claim 4 wherein the angle of the source normal varies between about 2° to 6° relative to the detector normal.

6. A system as in claim 1, wherein the frequency is caused to oscillate between about 3.2 MHz and 3.4 MHz.

7. A non-destructive inspection system for forming a substantially artifact free image of a test object, which system includes a source of ultrasonic energy to be directed at a test object;

a liquid crystal detector for receiving ultrasonic energy exiting the test object and providing a visual display;

a medium for coupling the source, the test object and the detector;

a first device for moving said source about a fixed pivot point that is substantially within said source whereby the normal to the source is caused to move through a small angle relative to the liquid crystal detector which minimizes disturbance of the medium due to movement of the source and cooperates in assuring an artifact-free image; and a second device for exciting said source so as to cause ultrasonic energy therefrom to oscillate between a pair of predetermined frequencies and scan the frequencies therebetween in a period of time sufficiently short to provide a flicker-free image;

wherein said device for moving said source is an eccentric which includes a disk and a link system;

wherein there is provided a housing within which the source and first device are enclosed so as to minimize coupling medium disturbance from movement of the source and which housing includes a window portion which is transparent to the ultrasonic energy so that an ultrasonic beam can be directed from the source to a position outside the housing;

wherein the normal is caused to move through a small angle between about 2° to 6°;

wherein the detector also defines a normal and said source normal and detector normal are oblique to each other and intersect at a small angle which varies between about 2° and 6°;

wherein the frequency is caused to oscillate between 3.2 megahertz and 3.4 megahertz; and wherein there is provided a third device for rotating said source about an axis extending through said pivot point and normal to the source.

8. A non-destructive inspection system for forming a substantially artifact-free image of a test object, which system includes:

a source of ultrasonic energy to be directed at a test object;

a liquid crystal detector for receiving ultrasonic energy exiting the test object and providing a visual display;

a medium for coupling the source a test object and the detector;

a first device for moving said source about a fixed pivot that is substantially within said source, whereby the normal to the source is caused to move through a small angle relative to the liquid crystal detector;

a second device for exciting said source so as to cause ultrasonic energy therefrom to oscillate between a pair of predetermined frequencies and scan the frequencies therebetween in a period of tine sufficiently short so as to provide a flicker free image; and a third device for rotating said source about an axis extending through said fixed pivot and normal to the source.

* * * * *